United States Patent [19]

Chu

[11] Patent Number: 5,102,399
[45] Date of Patent: Apr. 7, 1992

[54] CLINICAL TUBE HOLDER VALVE ASSEMBLY AND METHOD

[76] Inventor: Young K. Chu, 1065 Downshire Chase, Virginia Beach, Va. 23452

[21] Appl. No.: 536,292

[22] Filed: Jun. 11, 1990

[51] Int. Cl.$^5$ .............................................. A61M 5/00
[52] U.S. Cl. ................... 604/250; 604/180; 251/4; 138/106; 248/74.1; 248/205.3
[58] Field of Search ............. 604/246, 250, 174, 179, 604/180; 128/DIG. 26; 251/4; 248/74.1, 74.3, 205.3; 24/16 R, 16 PB; 138/106, 107

[56] References Cited

U.S. PATENT DOCUMENTS

| | | | |
|---|---|---|---|
| 2,716,013 | 8/1955 | Tinker | 251/4 |
| 2,995,334 | 8/1961 | Henderson et al. | 251/4 |
| 3,082,794 | 3/1963 | Wahl | 138/89 |
| 3,100,486 | 8/1963 | Nehring | 128/214 |
| 3,103,335 | 9/1963 | Martinez | 251/4 |
| 3,630,195 | 12/1971 | Santiomieri | 604/180 |
| 4,170,995 | 10/1979 | Levine et al. | 248/205.3 |

FOREIGN PATENT DOCUMENTS

| | | | |
|---|---|---|---|
| 2598625 | 11/1987 | France | 604/174 |
| 8502665 | 6/1985 | World Int. Prop. O. | 248/74.1 |

Primary Examiner—John D. Yasko
Assistant Examiner—Anthony Gutowski
Attorney, Agent, or Firm—Griffin, Branigan & Butler

[57] ABSTRACT

A clinical suction tube holder assembly (10), and a method of its use, involve the use of a receiver (12), having a wall (13), for defining a tube-receiving passage (18) attached to a mounting block (14) having pressure sensitive adhesive (16) thereon for selectively mounting the clinical suction tube holder assembly to a fixed structure at a support surface (36) on which a subject (40) to be treated is resting. After treating the subject with a fluid-flow tube (26) a portion thereof is selectively folded on itself and inserted into the tube receiving passage for being held therein at a fixed location with a blocked lumen (30) and for being selectively removed therefrom and unfolded, to thereby unblock its lumen, for further treatment.

8 Claims, 1 Drawing Sheet

CLINICAL TUBE HOLDER VALVE ASSEMBLY AND METHOD

This invention relates broadly to the art of clinical treatment, and more specifically to apparatus and methods used for treating subjects, in operating rooms, recovery rooms, and the like and even more specifically to the handling of fluid flow tubes.

When anesthetising patients, particularly in an operating room, it is often necessary to selectively use the ends of tubes attached to wall or mobile negative pressurized-fluid sources. For example, suction tubes are often used by anesthesiologists and other personnel for evacuating vomit, saliva, blood, and other body fluids. Normally, such a suction tube is attached to a negative-pressure source at an inner end thereof while an outer end is unobstructed. The negative-pressure source provides a continuous negative pressure at the outer end of the suction tube. This arrangement has the advantage that suction is readily available at the outer end without the necessity of using two hands to actuate valves, operate switches, and/or the like. That is, with such an arrangement, an operator can, with one hand, pick up the outer end of the suction tube and use it to remove fluids quickly. However, this arrangement does have some disadvantages. For one thing, when the suction tube is not in use, it continually sucks, thereby creating an objectionable noise and also possibly sucking up items it is not intended to evacuate. Another disadvantage of this arrangement is that when the outer end of the suction tube is not used, it is released by an operator and can fall on the floor or move to some other undesirable location. Not only might this contaminate the outer end of the suction tube but when an operator then again needs the outer end of the suction tube to treat a patient, he or she cannot easily find and/or reach it.

Thus, it is an object of this invention to provide a clinical suction tube holder assembly, as well as a method of using the same, which eliminates undesirable sucking noises when a suction tube is not in use, and which controls the position of the outer end of the suction tube so that it does not become contaminated and an operator can easily find, reach and/or access it.

In the past, operating room personnel have often overcome the difficulties described above by folding an end portion of such a suction tube on itself thereby crimping and closing a lumen of the suction tube. Such a folded portion of a suction tube has often been placed in gaps between clinical apparatus such as anesthesia machinery, under heavy apparatus, under operating table mattresses, or the like to prevent it from inadvertently unfolding. Although such procedures do eliminate undesirable sucking, they also have a number of difficulties. For one thing, the outer end of the suction tube is not always in a convenient location so that it can be quickly accessed when necessary. Also, such a contrivance is not always reliable, with the tube falling therefrom so that its lumen inadvertently opens, and its outer end becomes contaminated and/or cannot be easily found. Still further, since the folded portion of the tube can be placed in various locations, that is, between apparatus, under mattresses and the like, one sometimes forgets where he has placed the folded end of the tube and in an emergency, cannot readily find it even if it does not fall out. For all of these reasons, it is an object of this invention to provide a clinical suction tube holder assembly and a method of using the same which allows an operator to place a folded end of a clinical fluid-flow tube in a convenient location for quickly accessing the same. Likewise it is an object of this invention to provide such a clinical suction tube holder which is reliable in operation and which can be made to have a fixed location so that it can be easily found, accessed and/or reached.

A number of tube crimpers have been disclosed in U.S. Pat. Nos. 2,716,013 to Tinker, 2,995,334 to Henderson et al, 3,082,794 to Wahl, and 3,100,486 to Nehring. These patents disclose sleeves for receiving portions of tubing folded on themselves for thereby crimping these portions. U.S. Pat. Nos. 2,995,334 to Henderson et al and 3,100,486 to Nehring disclose such sleeves further attached to the tubes themselves. Although the tube holders of these patents would appear to have some advantages over methods which are in common practice in operating rooms, as are described above, they do not appear to be in common use. It is thought that perhaps a reason for this is that when these devices are used, ends of suction tubes are still not controlled. That is, if the ends of suction tubes are left unattended, they can still fall on the floor or to other undesirable locations where they may be difficult to locate. Also, the removal of such sleeves would appear to require two hands. Therefore, it is an object of this invention, to provide a clinical suction tube holder assembly, and a method of using the same, which controls the end of a clinical suction tube while closing its lumen so that it remains at a fixed location where it will not become contaminated and can be easily and quickly accessed by an operator with one hand.

Still further, it is an object of this invention to provide a disposable clinical suction tube holder which can be mounted to and dismounted from a structure without defacing the structure.

SUMMARY OF THE INVENTION

According to principles of this invention, a clinical suction tube holder assembly and a method of using the same involve the use of a receiver having a wall for defining a tube receiving passage and a mounting block for selectively mounting the receiver at a fixed location on a stationary structure located near a support surface on which a subject being treated is resting. In a preferred embodiment, the mounting block has a pressure-sensitive adhesive thereon. Also in a preferred embodiment, the receiver has a round tubular shape and the mounting block is affixed tangential to its outer surface.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
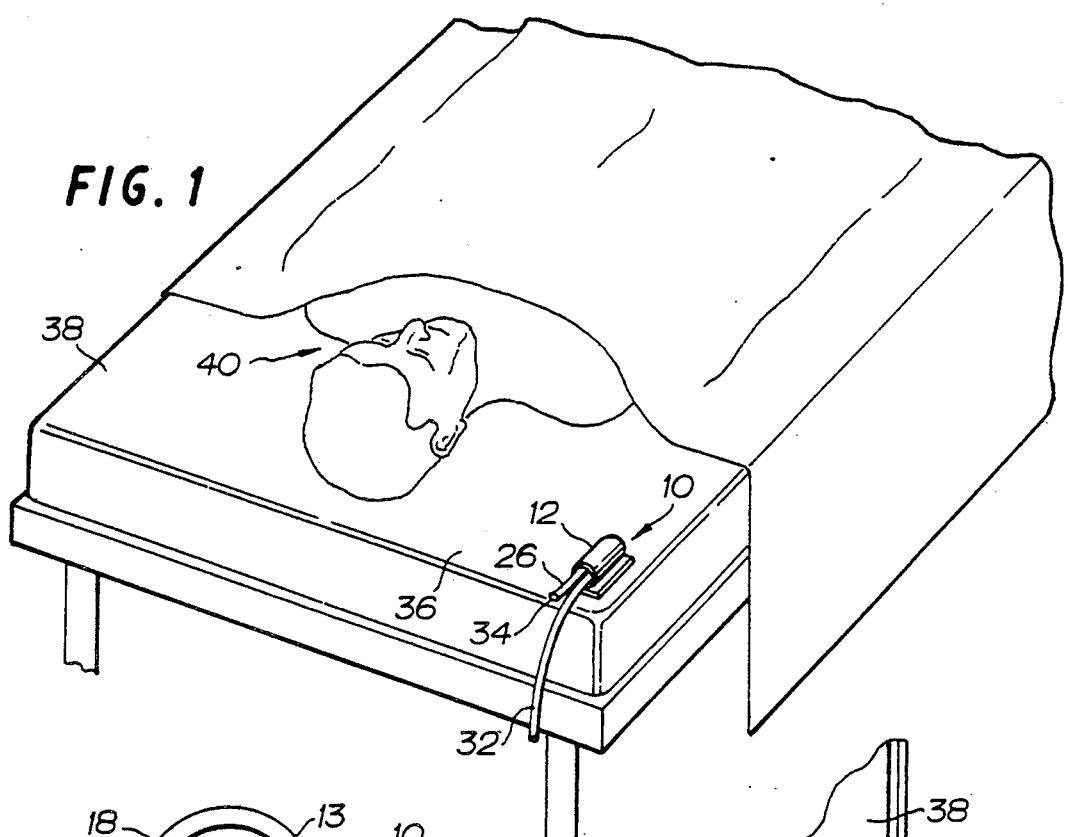
FIG. 1 is an isometric view of a clinical suction tube holder assembly of this invention mounted on an operating table with a patient thereon.

A suction tube holder assembly 10 of this invention comprises a receiver 12, a mounting block 14, and selective fastening material, which in the illustrated embodiment is a pressure-sensitive adhesive, 16.

The receiver 12 is basically a hard, rigid, resinous plastic tube stub having, in a preferred case, an internal diameter of ⅜" and a wall 13 with a thickness of 1/16 inch. In a preferred embodiment, the stub is approximately 1 inch long along its receiver passage or bore 18. A mounting block 14 is primarily of hard, rigid, resinous plastic with a top surface 20 thereof being fastened, or affixed, to an outer surface of the wall 13 by means of an adhesive, being molded therewith, being melted thereto, or the like, so as to be approximately tangential to the cylindrical outer surface 20 of the wall 13.

Figure 3:
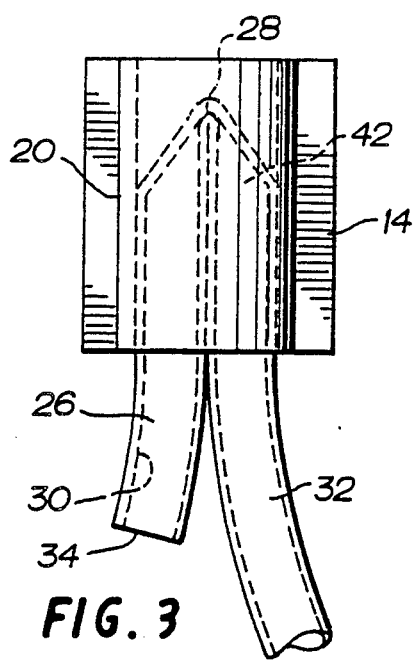
FIG. 3 is a top view of the clinical suction tube holder assembly of FIGS. 1 and 2.

As mentioned above, the selective fastening material 16 is a pressure sensitive adhesive which is on a bottom surface 22 of the mounting block 14 and which, before the clinical suction tube holder assembly 10 is to be used, is covered by an adhesive-protector sheet 24. The receiver passage 18 is sized to receive a folded normal operating room suction tube 26 which, when it is folded on itself as is depicted in FIG. 3, fully crimps a lumen portion 28, closing off a lumen 30 of the suction tube 26. An inner end 32 of the suction tube is fastened to vacuum equipment (not shown) for creating a suction in the lumen 30 of the suction tube 26 to thereby create a negative pressure at an open outer end 34 of the suction tube 26. However, when the suction tube 26 is crimped as is shown in FIG. 3, the suction cannot pass the lumen portion 28 and, therefore, there is no negative pressure at the open outer end 34.

Figure 2:
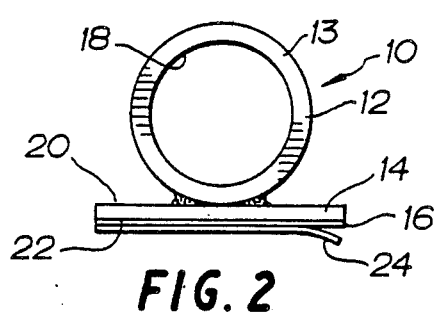
FIG. 2 is an end view of the clinical suction tube holder assembly of FIG. 1.
Figure 2A:
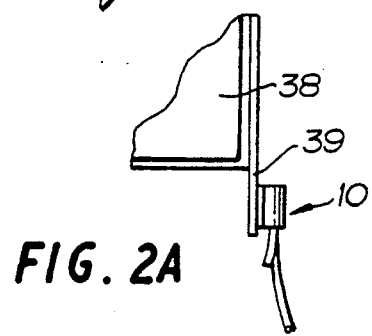
FIG. 2A is a segmented top view of a portion of a different operating table on which a clinical suction tube holder of this invention is mounted.

When using the clinical suction tube holder assembly 10 of this invention, the adhesive-protector sheet 24 is removed and the pressure-sensitive adhesive 16, or "stickum", which forms the selective fastening material 16, is stuck to a structural support surface 36, which in the case of FIG. 1 is the top of an operating table mattress 38. However, it will be easily understood by those of ordinary skill in the art that the clinical suction tube holder assembly 10 is not limited to being attached directly on an operating table mattress, but rather can be attached to an operating-table frame 39 (see FIG. 2A) as well as to other stationary structures near an operating table. When it is desired to treat a subject or patient 40, the vacuum equipment (not shown) on the inner end of the suction tube 26 is turned on, thereby creating a negative pressure at the open outer end 34. This open outer end 34 is placed in body cavities or wherever it is needed to evacuate fluids. However, when the suction tube 26 is not in use, an outer end portion 42 thereof is folded back on itself so as to create a crimp at the lumen portion 28, thereby closing off the lumen 30. When this is done, negative pressure no longer appears at the open outer end 34 and there is no sucking noise. The folded portion 42 is inserted into the receiver passage or bore 18 of the receiver 12 as is depicted in FIG. 3.

Once an operation has been completed, or at least after one session of operations, the clinical suction tube holder assembly is normally removed and discarded, with new ones being used for later operations. In this regard, fixed structures to which the clinical suction tube holder are attached are different for different operations, depending on locations and orientations of patients. Also, structures to which clinical suction tube holders are attached must often be cleaned and made steril between operations.

Figure 4:
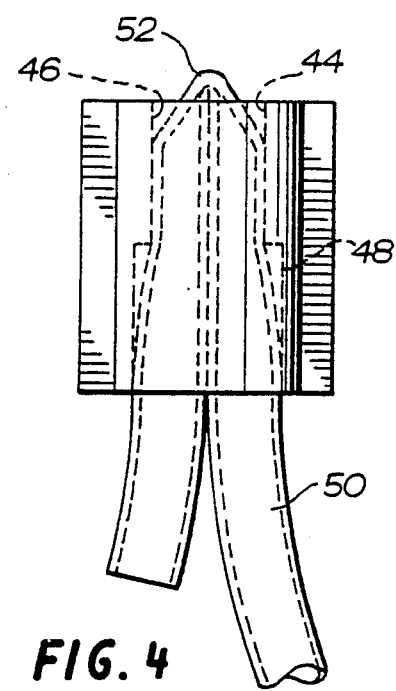
FIG. 4 is a top view of a second embodiment clinical suction tube holder of this invention.

FIG. 4 depicts an alternate embodiment of this invention in which a receiver passage or bore 44 has a smaller portion 46 and a larger portion 48. The smaller portion has a smaller diameter than the larger portion 48 so that it will receive and maintain folded a smaller suction tube 50 than will the larger portion 48. With this "stepped passage" arrangement, the receiver passage 44 can be used with suction tubes 50 of various sizes. If a larger suction tube is used than the one depicted in FIG. 4, a folded portion 52 thereof is not inserted all the way through the larger portion 48 into the smaller portion 46 as is shown, but rather, only extends through the larger portion 48 and remains crimped therein. It should be understood that the passage 44 could have more than two stepped portions.

It will be understood by those of ordinary skill in the art that a clinical suction tube holder assembly which comprises a receiver for receiving a folded, crimped, tube with selective fastening material, such as an adhesive, thereon is tremendously beneficial in an operating-room or recovery room because it allows a clinical suction tube holder assembly to be mounted at a fixed position whoes location is selectively chosen for each new procedure. The fixed position is normally chosen so that the open outer end of the suction tube can be quickly accessed by clinical personnel when needed. Also, it is beneficial when appropriate clinical personnel know where this fixed location is so that the suction tube can be quickly found when needed. Still further, by fixing the clinical suction tube holder assembly 10 in a selected position with the use of a mounting block and selective fastening material, such as pressure sensitive adhesive, it is possible for clinical personnel to remove and replace a crimped tube with one hand, thereby leaving the other hand free for holding and/or manipulating other things. Further, the combination of this invention provides a more reliable crimping of a suction tube than is the case when a suction tube is held crimped under a mattress, between apparatus, and the like. Also, the combination of elements for this invention is highly beneficial because it holds the outer end of a suction tube secure from falling or otherwise from being pulled to an undesirable location, such as on a floor.

While the invention has been particularly shown and described with reference to a preferred embodiment, it will be understood by those skilled in the art that various changes in form and detail may be made therein without departing from the spirit and scope of the invention. For example, it would be possible to close off the end of the tubularly-shaped receiver 12 and place a mounting block on a cover closing off the end. In fact, the cover itself could be the mounting block, although such a mounting block, if too small, may not be strong enough for withstanding pulls which sometimes occur on suction tubes.

It would also be possible to make the tubularly-shaped receiver 12 and/or the mounting block 14 of resilient resinous plastic. By making the mounting block 14 of resilient plastic, its bottom surface 22 can more easily conform to irregularly shaped surfaces for adhering thereto.

Also, longitudinal ribs could be placed on an inner surface of the receiver forming the receiver passage for guiding the folded suction tube in place and preventing its rotation within the receiver.

The embodiments of the invention in which an exclusive property or privilege are claimed or defined as follows:

1. A clinical tube holder assembly for holding a clinical fluid-flow tube used for selective treatment of a subject at a location on a support surface while limiting passage of fluid material flowing through a lumen of the tube, said tube holder comprising:

a receiver having a wall means for defining a tube receiving passage of lateral dimensions for snugly receiving and retaining a portion of said clinical flow through tube which is folded back upon itself so as to close said lumen, thereby preventing passage of fluid material therethrough; and a mounting means attached to said receiver for selectively mounting said receiver to a fixed structure at a fixed position relative to said fixed structure near said location on said support surface, said mounting means includes a relatively flat mounting block having fastening material on one side thereof and said receiver on he other side thereof, said receiver being tubular in cross-section, having a tubular shape, while said mounting block is attached on an outside surface of the tubularly shaped receiver approximately tangential to said outside surface;

whereby said tube holder assembly can be selectively mounted to said fixed structure near said location on said support surface and a portion of said clinical tube can be selectively folded on itself and inserted into said tube receiving passage for being held at said location on said support surface and for being selectively removed from said receiving passage, unfolded, and used for treatment.

2. A clinical tube holder assembly as in claim 1 wherein said fastening material is pressure-sensitive adhesive.

3. A clinical tube holder assembly as in claim 1 wherein said tube receiving passage has at least two sizes stepped axially or laterally from one another so that said tube receiving passage can receive and crimp clinical suction tubes of different sizes.

4. A clinical tube holder assembly as in claim 1 wherein said mounting means has the function of maintaining said receiver mounted to said fixed structure at said fixed position in such a sufficiently stable manner that a folded tube can be removed therefrom and an unfolded tube can be folded and inserted thereinto with one hand.

5. A method of treating a patient with fluid comprising the steps of:

fixedly attaching a separate receiver for defining a tube-receiving passage of a size for snugly receiving and retaining a portion of a clinical fluid tube which is folded upon itself so as to close a lumen of the tube at a fixed position to a fixed support near said patient;

treating said patient with an open outer end of said tube by means of fluid passing through the lumen of said tube;

folding a portion of said tube on itself to crimp said lumen of said tube and inserting said folded portion in the passage of said receiver for holding said tube to said fixed support at said fixed position with said lumen closed.

6. A method of treating a patient as in claim 5 wherein said step of affixing said receive to said fixed support near said support table includes the substep of adhering said receiver to said fixed support with an adhesive.

7. A method of treating a patient as in claim 5 wherein is further included the step of detaching the separate receiver from said fixed support upon completion of treatment of said patient.

8. A method of treating a patient as in claim 5 wherein said folding and inserting steps are accomplished by clinical personnel with one hand.

* * * * *